United States Patent
Jain et al.

(10) Patent No.: US 10,913,906 B2
(45) Date of Patent: Feb. 9, 2021

(54) PROCESS FOR SEPARATION OF AROMATIC HYDROCARBONS FROM A MIXED HYDROCARBON STREAM

(71) Applicant: SABIC Global Technologies B.V., Bergen op Zoom (NL)

(72) Inventors: Kokil Jain, Cheshire (GB); Christoph Dittrich, Geleen (NL); Kumar Prashant, Altrincham (GB)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 382 days.

(21) Appl. No.: 16/061,391

(22) PCT Filed: Dec. 12, 2016

(86) PCT No.: PCT/EP2016/080624
§ 371 (c)(1),
(2) Date: Jun. 12, 2018

(87) PCT Pub. No.: WO2017/102641
PCT Pub. Date: Jun. 22, 2017

(65) Prior Publication Data
US 2019/0040325 A1  Feb. 7, 2019

(30) Foreign Application Priority Data
Dec. 14, 2015 (EP) .................... 15199881

(51) Int. Cl.
*C10G 53/04* (2006.01)
*C10G 45/68* (2006.01)
(Continued)

(52) U.S. Cl.
CPC ............... *C10G 53/04* (2013.01); *C07C 7/11* (2013.01); *C10G 21/14* (2013.01); *C10G 21/28* (2013.01);
(Continued)

(58) Field of Classification Search
CPC ........... C07C 7/11; C07C 15/00; C10G 21/14; C10G 21/28; C10G 2300/1096;
(Continued)

(56) References Cited

U.S. PATENT DOCUMENTS 4,299,667 A  11/1981 Klein et al.
5,422,007 A * 6/1995 Nicoud .............. B01D 15/1842
  210/659
(Continued)

FOREIGN PATENT DOCUMENTS

CN  101821359 A  9/2010
CN  102046760 A  5/2011
(Continued)

OTHER PUBLICATIONS

European Search for European Application No. 15199881.2; dated May 9, 2016; 7 pages.
(Continued)

*Primary Examiner* — Cabrena Holecek
(74) *Attorney, Agent, or Firm* — Cantor Colburn LLP

(57) ABSTRACT

The present invention relates to a process for the separation of aromatic hydrocarbons from a hydrocarbon feed stream comprising contacting a hydrocarbon feed stream with a solvent for aromatics (aromatics solvent) to provide an aromatics-laden solvent stream and subjecting the aromatics-laden solvent stream to solvent regeneration to provide regenerated aromatics solvent and an aromatics stream.

19 Claims, 3 Drawing Sheets

(51) Int. Cl.
*C10G 21/14* (2006.01)
*C10G 31/06* (2006.01)
*C10G 21/28* (2006.01)
*C07C 7/11* (2006.01)

(52) U.S. Cl.
CPC .............. *C10G 31/06* (2013.01); *C10G 45/68* (2013.01); *C10G 2300/1096* (2013.01); *C10G 2300/4081* (2013.01); *C10G 2400/30* (2013.01)

(58) Field of Classification Search
CPC ........ C10G 2300/4081; C10G 2400/30; C10G 31/06; C10G 45/68; C10G 53/04
See application file for complete search history.

(56) References Cited

U.S. PATENT DOCUMENTS

| | | | |
|---|---|---|---|
| 2008/0047872 A1 | 2/2008 | Iaccino et al. | |
| 2009/0253934 A1* | 10/2009 | Ho | C07C 51/44 562/600 |
| 2016/0002162 A1* | 1/2016 | Tanzio | C10G 1/08 548/469 |

FOREIGN PATENT DOCUMENTS

| | | | | |
|---|---|---|---|---|
| EP | 0736588 A2 | * | 10/1996 | ............... C10G 7/08 |
| EP | 0736588 A2 | | 10/1996 | |
| WO | 2007123977 A2 | | 11/2007 | |
| WO | 2015047085 A1 | | 4/2015 | |
| WO | 2016004248 A2 | | 1/2016 | |

OTHER PUBLICATIONS

International Search Report for International Application No. PCT/EP2016/080624; dated Feb. 1, 2017; 4 pages.
Shudo, Yukoh et al.; "Exergy analysis of the demonstration plant for co-production of hydrogen and benzene from biogas"; International Journal of Hydrogen Energy, 2009, vol. 34, pp. 4500-4508.
Written Opinion of the International Search Report for International Application No. PCT/EP2016/080624; dated Feb. 1, 2017; 6 pages.
EP Office Action Application No. 16806197.6; dated Mar. 20, 2019; pp. 7.

* cited by examiner

PROCESS FOR SEPARATION OF AROMATIC HYDROCARBONS FROM A MIXED HYDROCARBON STREAM

CROSS REFERENCE TO RELATED APPLICATIONS

This application is a 371 of International Application No. PCT/EP2016/080624, filed Dec. 12, 2016, which claims priority to European Application No. 15199881.2, filed Dec. 14, 2015, both of which are incorporated herein by reference in their entirety.

The present invention relates to a process for the separation of aromatic hydrocarbons from a gaseous hydrocarbon feed stream comprising contacting a hydrocarbon feed stream with a solvent for aromatics (aromatics solvent) to provide an aromatics-laden solvent stream and subjecting the aromatics-laden solvent stream to solvent regeneration to provide regenerated aromatics solvent and an aromatics stream.

Naphthalene is the main hydrocarbon side product of the aromatization of light alkanes, e.g. methane, ethane, propane and butanes. Other hydrocarbon (side) products include ethylene, ethane, propane, benzene, toluene, xylenes and (in very small quantities) substituted polyaromatics such as $\alpha$- and $\beta$-methyl naphthalene.

Processes for the separation of aromatic hydrocarbons from a mixed hydrocarbon stream, such as a stream produced by the aromatization of light alkanes, have been previously described. For instance, WO2007/123977A2 and Shudo et al. (2009) Int. J. Hydr. En. Vol. 34, pp. 4500-4508 describe that benzene and heavier hydrocarbons in the reactor effluent are conventionally separated from lighter hydrocarbons, unconverted feedstock and co-product hydrogen by cooling, condensation and absorption with a liquid solvent. Absorption is chosen as separation method because cooling and condensation alone is not sufficient to recover most of the product benzene as condensate because of the high molar fraction of non-condensable gases in the reactor effluent. Very low (cryogenic) condensation temperatures would be required for condensing most of the benzene product which would solidify below 5° C.

$\alpha$-methyl naphthalene (with a melting point of −31° C. and a boiling point of 245° C. at ambient pressure) or tetralin (with a melting point of −36° C. and a boiling point of 208° C. at ambient pressure) are suitable solvents for the absorption of benzene and higher aromatics, including naphthalene.

Absorption of gases requires the solvents to be in a liquid state, so the reactor effluent needs to be cooled from reactor temperature (usually above 500° C.) to a temperature at which the solvent is a liquid and has sufficiently high absorption capacity. Additionally, the reactor effluent is compressed in order to further increase the absorption capacity, and to reduce the specific volume of the not absorbed constituents of the reactor effluent.

The major side-product naphthalene is one of the first hydrocarbons that should condense out of the gas phase, but its high melting point (80° C. at ambient pressure) implies that naphthalene desublimates as a solid during cooling and compression at typical temperature and pressure conditions of a subsequent absorption unit operation. This will happen even if naphthalene is diluted by non-condensable gases and lower boiling hydrocarbons. Fouling of heat exchangers by a layer of solid naphthalene and even plugging of lines are the consequence of desublimation of solid naphthalene instead of condensation of a liquid hydrocarbon.

Desublimation of solid naphthalene from the reactor effluent during cooling and compression can be avoided by keeping the effluent always above 80° C. instead of cooling it to temperatures above cooling water temperature. Keeping the effluent above 80° C. hence increases the specific work for compression because of the higher specific gas volume at higher temperature, and generally increases the required compressor size and thus cost.

It was an object of the present invention to provide an improved process for the separation of aromatic hydrocarbons from a mixed hydrocarbon stream which prevents desublimation of naphthalene without having to keep the naphthalene-containing streams at a temperature of above 80° C.

The solution to the above problem is achieved by providing the embodiments as described herein below and as characterized in the claims. Accordingly, the present invention provides a process for the separation of aromatic hydrocarbons from a hydrocarbon feed stream comprising the steps of:

(a) contacting a gaseous hydrocarbon feed stream with aromatics solvent to provide a gaseous hydrocarbon-solvent mixture;

(b) reducing the temperature of the gaseous hydrocarbon-solvent mixture to a temperature wherein the aromatics solvent is at least partially in liquid phase and the not absorbed hydrocarbons are in gas phase;

(c) subjecting the thus obtained cooled hydrocarbon-solvent mixture to separation to provide an aromatics-laden solvent stream and a gaseous stream; and (d) subjecting the aromatics-laden solvent stream to solvent regeneration to provide regenerated aromatics solvent and an aromatics stream.

In the context of the present invention, it was surprisingly found that desublimation of naphthalene in a process for the separation of aromatic hydrocarbons in a hydrocarbon feed can be prevented by contacting a gaseous aromatics-comprising feed with aromatics solvent to provide a gaseous hydrocarbon-solvent mixture followed by reducing the temperature of the gaseous hydrocarbon-solvent mixture to a temperature wherein the aromatics solvent is at least partially in liquid phase and the not absorbed hydrocarbons are in gas phase which allows the separation of an aromatics-laden solvent stream and a gaseous stream. In the presence of the aromatics solvent, the naphthalene co-condenses with the aromatics solvent when the temperature of the gaseous hydrocarbon-solvent mixture is reduced to a temperature that is below the dew point of the aromatics solvent, thereby keeping the naphthalene in solution in the aromatics solvent since naphthalene is very well soluble in the aromatics solvent. Accordingly, the flow rate of the aromatics solvent should be selected as such that the condensed naphthalene can be readily dissolved in the aromatics solvent, to prevent the formation of solids due to saturation of the aromatics solvent with naphthalene.

Processes for the separation of aromatic hydrocarbons from a hydrocarbon feed stream are well known from the art. These processes, however, do not comprise the steps of first contacting a gaseous hydrocarbon feed stream with aromatics solvent to provide a gaseous hydrocarbon-solvent mixture followed by a step of reducing the temperature of the gaseous hydrocarbon-solvent mixture to a temperature wherein the aromatics solvent is at least partially in liquid phase and the not absorbed hydrocarbons are in gas phase.

WO 2015/047085 A1 describes a process for the preparation of aromatic compounds from a feed stream comprising biomass or mixtures of biomass and synthetic polymer.

WO 2015/047085 A1 further describes that a vapour stream containing aromatics is contacted with hydrocarbon solvent inside a spray tower-like absorption column, wherein absorption and condensation of the target components occur simultaneously in the same unit operation.

EP 0 736 588 A2 describes a process for removing aromatic hydrocarbons from hydrocarbon vapour streams. In the process according to EP 0 736 588 A2, a hydrocarbon vapour containing aromatics is condensed for the biggest part inside an extractive distillation column. Aromatics are extracted from liquid hydrocarbon phase by the solvent and absorbed by the solvent from the non-condensable vapour fraction, both inside an extractive distillation column where the condensable hydrocarbon fraction was liquefied.

Shudo Yukoh et al (2008) Int J Hydrogen Energy 34(10) pp 4500-4508 describes a process wherein a vapour effluent from a methane dehydroaromatization process is quenched by spraying 1-methyl naphthalene into a column called quenching pot.

Shudo Yukoh et al. does not describe in which phase the products leave the quenching pot.

U.S. Pat. No. 4,299,667 A describes a process for recovering pure benzene from hydrocarbon mixtures containing the same and non-aromatic compounds. In the process according to U.S. Pat. No. 4,299,667 A, a hydrocarbon vapour containing aromatics is contacted with solvent inside a scrubber/spray condenser-type unit operation.

US 2008/047872 A1 describes a method for converting methane to liquid hydrocarbons, including aromatic hydrocarbons. US 2008/047872 A1 generically describes that solvent extraction may be used as a separation process.

The term "aromatic hydrocarbons" or "aromatics" is very well known in the art. Accordingly, the term "aromatic hydrocarbon" relates to cyclically conjugated hydrocarbon with a stability (due to delocalization) that is significantly greater than that of a hypothetical localized structure (e.g. Kekulé structure). The most common method for determining aromaticity of a given hydrocarbon is the observation of diatropicity in the $^1$H NMR spectrum, for example the presence of chemical shifts in the range of from 7.2 to 7.3 ppm for benzene ring protons. As used herein, the term "polyaromatics" or "polyaromatic hydrocarbons" relates to a mixture of aromatic hydrocarbons having more than one aromatic ring. As used herein, the term "monoaromatic hydrocarbons" or "monoaromatics" relates to a mixture of aromatic hydrocarbons having only one aromatic ring.

The term "BTX" as used herein relates to a mixture of benzene, toluene and xylenes.

As used herein, the term "C# hydrocarbons", or "C#", wherein "#" is a positive integer, is meant to describe all hydrocarbons having # carbon atoms. Moreover, the term "C#+ hydrocarbons" is meant to describe all hydrocarbon molecules having # or more carbon atoms. Accordingly, the term "C9+ hydrocarbons" is meant to describe a mixture of hydrocarbons having 9 or more carbon atoms. The term "C9+ alkanes" accordingly relates to alkanes having 9 or more carbon atoms.

The term "LPG" as used herein refers to the well-established acronym for the term "liquefied petroleum gas". LPG generally consists of a blend of C2-C4 hydrocarbons i.e. a mixture of C2, C3, and C4 hydrocarbons.

In step (a) of the process of the present invention a gaseous hydrocarbon feed stream is contacted with aromatics solvent to provide a gaseous hydrocarbon-solvent mixture.

Preferably, step (a) of the process of the present invention comprises spraying liquid aromatics solvent into the gaseous hydrocarbon feed stream, wherein the gaseous hydrocarbon feed stream has a higher temperature than the aromatics solvent, thereby evaporating said aromatics solvent. This has the advantage that good mixing and evaporation of the aromatics solvent and the gaseous hydrocarbon feed is achieved. Furthermore, the gaseous hydrocarbon feed stream is cooled this way, depending on the aromatics solvent flow rate to the reactor effluent and the aromatics solvent heat of evaporation. The aromatics solvent flow rate to the hydrocarbon feed stream may be chosen large enough to saturate the gaseous hydrocarbon-solvent mixture to its dew point at the inlet of the subsequent cooling step. This will decrease the required heat transfer area due to better heat transfer during condensation as compared to heat transfer from gas.

The aromatics solvent is used for separating the gaseous hydrocarbon feed into aromatics and light gases. Accordingly, the aromatics solvent useful in the process of the present invention may be any solvent in which aromatic hydrocarbons have a better solubility than the other components comprised in the hydrocarbon-comprising feed stream. Suitable aromatics solvent furthermore must have a boiling point high enough to prevent condensation of naphthalene without condensation of the aromatics solvent, and a melting point low enough to prevent solidification of the condensed mixture of naphthalene and aromatics solvent. The aromatics solvent used in the process of the present invention preferably has a boiling point of 200° C. or higher at ambient pressure, more preferably a boiling point of 218° C. or higher at ambient pressure. The aromatics solvent used in the process of the present invention preferably has a melting point of 35° C. and lower at ambient pressure, more preferably a melting point of −0° C. or lower at ambient pressure.

The aromatics solvent used in the process of the present invention preferably is selected from the group consisting of methyl naphthalene, ethyl naphthalene, propyl naphthalene, di-methyl naphthalene, methyl ethyl naphthalene, di-ethyl naphthalene, methyl propyl naphthalene, ethyl propyl naphthalene, di-propyl naphthalene, tetralin, decalin, toluene, xylenes, decane, undecane, dodecane, tridecane, tetradecane and sulfolane.

The hydrocarbon feed stream used in the process of the present invention may be any mixed hydrocarbon stream, comprising aromatic hydrocarbons and (preferably) naphthalene. Accordingly, the present invention provides a process for the separation of aromatic hydrocarbons from a hydrocarbon feed stream comprising naphthalene, the process comprising the steps of:

(a) contacting a gaseous hydrocarbon feed stream with aromatics solvent to provide a gaseous hydrocarbon-solvent mixture;

(b) reducing the temperature of the gaseous hydrocarbon-solvent mixture to a temperature wherein the aromatics solvent is at least partially in liquid phase and the not absorbed hydrocarbons are in gas phase;

(c) subjecting the thus obtained cooled hydrocarbon-solvent mixture to separation to provide an aromatics-laden solvent stream and a gaseous stream; and (d) subjecting the aromatics-laden solvent stream to solvent regeneration to provide regenerated aromatics solvent and an aromatics stream.

Preferably, the hydrocarbon feed stream used in the process of the present invention comprises at least 0.1 mass-% naphthalene but not more than 10 mass-% naphthalene, more preferably at least 0.1 mass-% naphthalene but not more and 5 mass-% naphthalene and most preferably at least 0.1 mass-% naphthalene but not more than 1 mass-% naphthalene.

Preferably, the gaseous hydrocarbon feed stream used in the process of the present invention is produced by alkane aromatization, preferably by methane dehydroaromatization. Such processes are well known to produce monoaromatics, such as benzene, and polyaromatics, such as naphthalene.

In one embodiment, the feed of the process of the present invention comprises as a side-product a component, which functions as an aromatics solvent as defined in the present invention. For instance, a hydrocarbon feed produced by a methane aromatization process may comprise methyl naphthalenes. When using such a hydrocarbon feed in the process of the present invention, the aromatics solvent is already partially comprised in the hydrocarbon feed and thus less fresh aromatics solvent needs to be added to the gaseous hydrocarbon feed stream to provide the gaseous hydrocarbon-solvent mixture.

Preferably, the gaseous hydrocarbon feed stream used in the present invention comprises at least 1 wt-% aromatic hydrocarbons and preferably at least 5 wt-% aromatic hydrocarbons.

In step (b) of the process of the present invention the temperature of the gaseous hydrocarbon-solvent mixture is reduced to a temperature wherein the aromatics solvent is at least partially in liquid phase and the not-absorbed hydrocarbons are in gas phase.

Preferably, the temperature of the gaseous hydrocarbon-solvent mixture in step (b) is reduced to 25-70° C., more preferably to 40-65° C. and most preferably to 55-60° C. Accordingly, the temperature of the gaseous hydrocarbon-solvent mixture in step (b) is preferably reduced to 25-70° C., for example at least 40° C. or at least 55° C. and/or at most 65° C. or at most 60° C.

In step (c) of the process of the present invention the obtained cooled hydrocarbon-solvent mixture is subjected to separation to provide an aromatics-laden solvent stream and a gaseous stream.

Preferably, the separation in step (c) comprises gas-liquid separation. Any conventional means for obtaining gas-liquid separation may be used in the process of the present invention, such as a gravity settling chamber, demister internals like zig-zag baffles or demister pads, electrostatic precipitator, cyclone or a centrifugal separator.

Preferably, the gaseous stream obtained by gas-liquid separation in step (c) of the present process is subjected either to:
at least one further cooling step; or
a compression step, optionally with another subsequent cooling step, and subjecting the thus obtained cooled or compressed, or optionally cooled and compressed stream, to a second gas-liquid separation to provide a further aromatics-laden solvent stream and a second gaseous stream. By subjecting the gaseous stream obtained by gas-liquid separation to further compression and/or cooling and subjecting the thus obtained cooled stream to a second gas-liquid separation, further remaining aromatics solvent which was contained in the gaseous stream, preferably obtained from first gas-liquid separation, can be condensed, together with remaining aromatics contained in said gaseous stream. The thus obtained further aromatics-laden solvent stream may be combined with the other aromatics-laden solvent streams that are subjected to solvent regeneration.

The gaseous stream may be compressed in stages in order to limit the temperature rise in each stage due to compression, and thereby cooled between each stage. Consequently, there might be different locations with conditions for co-condensing naphthalene and aromatics solvent in the process. The condensate should contain enough aromatics solvent at each of those locations in order to prevent the deposition of solid naphthalene leading to deposits and fouling. This may be achieved by choosing the aromatics solvent flow rate large enough such that the aromatics solvent's dew point is not below the dew point of naphthalene. Preferably, the gaseous stream obtained by gas-liquid separation in step (c) of the present process is subjected to a compression step followed by at least one cooling step, wherein the compression step comprises a first compression stage after which the partially compressed stream is contacted with aromatics solvent and the thus obtained mixture is subjected to a gas-liquid separation to provide a further aromatics-laden solvent stream and a partially compressed gaseous stream that is subsequently subjected to a second compression stage. When compressing the gaseous stream, remaining traces of naphthalene in the gaseous stream may desublimate and form fouling deposits. To prevent such fouling, the partially compressed stream may be contacted with additional aromatics solvent prior to compression to provide a further aromatics-laden solvent stream after gas-liquid separation. The compression step comprised in the process of the present invention may comprise more than two compression stages. Moreover, the process of the present invention comprising more than two compression stages may comprise more than one instances wherein partially compressed streams are contacted with aromatics solvent and the thus obtained mixture is subjected to a gas-liquid separation to provide further aromatics-laden solvent stream and partially compressed gaseous stream that is subsequently subjected to a further compression stage.

Preferably, the gaseous stream obtained by gas-liquid separation in step (c) of the present process is subjected to a compression step followed by at least one cooling step, wherein between the compression step and the cooling step additional aromatics solvent is fed to the compressed stream. By contacting the fully compressed gaseous stream with aromatics solvent, a further aromatics-laden solvent stream may be obtained when said compressed gaseous stream is cooled to a temperature wherein the aromatics solvent is at least partially condensed and the thus obtained gas-liquid mixture is subjected to a further gas-liquid separation. Such an additional step is useful to further reduce the aromatics content of the compressed gaseous stream.

Preferably, the gaseous stream obtained by gas-liquid separation is subjected to a compression step followed by at least one cooling step, wherein the thus obtained compressed and cooled stream has a pressure of 1500-4000 kPa, more preferably of 2000-3500 kPa and most preferably of 2500-3000 kPa and a temperature of 20-50° C., more preferably of 25-45° C. and most preferably of 30-40° C. Accordingly, the gaseous stream obtained by gas-liquid separation in step (C) is subjected to compression and cooling to a pressure of preferably 1500-4000 kPa, for example at least 2000 kPa or at least 2500 kPa and/or at most 3000 kPa or at most 3000 kPa. Moreover, the gaseous stream obtained by gas-liquid separation in step (C) is subjected to compression and cooling to a temperature of preferably 20-50° C., for example at least 25° C. or at least 30° C. and/or at most 45° C. or at most 40° C.

Preferably, the gaseous stream is contacted with aromatics solvent in an aromatics absorption column to provide a further aromatics-laden solvent stream and an aromatics free effluent. This "gaseous stream" that is contacted with aromatics solvent in an aromatics absorption column thus is the gaseous stream obtained in step (C) of the present invention, which, in more specific embodiments of the present invention, may further be subjected to compression, and/or cooling, and/or contacted with additional aromatics solvent before being contacted with additional aromatic solvent in the aromatics absorption column. The gaseous stream, which optionally may be subjected to compression, and/or cooling, and/or contacted with additional aromatics solvent as described herein, thus may be subsequently subjected to aromatics solvent absorption in an aromatics absorption column.

In step (d) of the process of the present invention the aromatics-laden solvent stream is subjected to solvent regeneration to provide regenerated aromatics solvent and an aromatics stream.

Preferably, the regenerated aromatics solvent obtained in step (d) is recycled to the aromatics solvent used in the process. Accordingly, the process of the present invention may comprise a closed loop wherein the aromatics solvent used in the process is provided by the solvent regeneration. The aromatics solvent loop may comprise a purge stream to remove heavy components from the process of the present invention. Fresh aromatics solvent is added to the aromatics solvent loop in order to replenish the aromatics solvent purged with the heavy components.

Preferably, aromatics solvent provided by the solvent regeneration is recycled to the aromatics absorption column.

The aromatics solvent flow rate to the gaseous stream upstream of the aromatics absorption column can be partially decoupled from the aromatics solvent absorption-regeneration loop originating from the aromatics absorption column by a short solvent cycle with additional cooling. The liquid solvent-naphthalene mixture collected from the gas-liquid separators downstream of the effluent cooler(s) is cooled and recycled to the aromatics solvent dosing points to the gaseous stream upstream of the aromatics absorption column. Only a portion of naphthalene-laden solvent is returned to the solvent regeneration column and made up by regenerated solvent. A high solvent flow rate to the gaseous stream can be maintained this way without unreasonably increasing the energy demand for solvent regeneration. Also, lower compressor inlet temperatures can be achieved which leads to lower required specific compression work and smaller compressor size.

In one embodiment of the present invention, accordingly, the entire aromatics-laden solvent stream obtained from the aromatics absorption column is subjected to solvent regeneration, whereas only a portion of the aromatics-laden solvent stream obtained from the one or more gas-liquid separation steps upstream from the aromatics absorption column is subjected to solvent regeneration.

Preferably, one or more of the aromatics-laden solvent streams are only partially subjected to solvent regeneration, wherein the remaining part of said one or more aromatics-laden solvent streams that are not subjected to solvent regeneration are cooled and recycled to the aromatics solvent, for instance via line (20). Accordingly, the process of the present invention may comprise a loop wherein the aromatics solvent used in the process is partially provided by the solvent regeneration.

The remaining part of the one or more aromatics-laden solvent streams that are not subjected to solvent regeneration preferably are used as the aromatics solvent feed.

In a further aspect, the present invention also relates to a process installation suitable for performing the process of the invention. This process installation and the process as performed in said process installation is presented in FIGS. 1-3.

Accordingly, the present invention provides a process installation for the separation of aromatic hydrocarbons from a hydrocarbon feed stream (1) comprising:

cooler (A) in which the temperature of a gaseous hydrocarbon-solvent mixture is reduced to a temperature wherein the aromatics solvent is at least partially in liquid phase and the not-absorbed hydrocarbons are in gas phase;

separator (B) in which the thus obtained cooled hydrocarbon-solvent mixture (3) is subjected to a separation to provide an aromatics-laden solvent stream (4) and a gaseous stream; and solvent regeneration column (C) in which the aromatics-laden solvent stream (4) is subjected to solvent regeneration to provide regenerated aromatics solvent (13) and an aromatics stream (14).

It is noted that the invention relates to all possible combinations of features described herein, particularly features recited in the claims.

It is further noted that the term "comprising" does not exclude the presence of other elements. However, it is also to be understood that a description on a product comprising certain components also discloses a product consisting of these components. Similarly, it is also to be understood that a description on a process comprising certain steps also discloses a process consisting of these steps.

Figure 1:
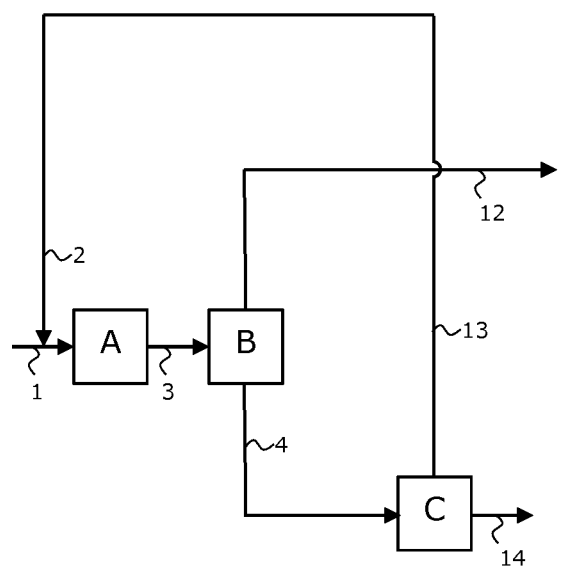
FIG. 1: The gaseous hydrocarbon feed stream (1) is contacted with aromatics solvent (2) to provide a gaseous hydrocarbon-solvent mixture that is sent to cooler (A) in which a mixed hydrocarbon-solvent stream (3) is generated with a temperature at which the aromatics solvent is at least partially in liquid phase and the not absorbed hydrocarbons are in gas phase. Stream (3) is sent to separator (B) in which the thus obtained cooled hydrocarbon-solvent mixture (3) is subjected to a separation to provide an aromatics-laden solvent stream (4) and a gaseous stream (12). The thus obtained aromatics-laden solvent stream (4) is subjected to solvent regeneration in solvent regeneration column (C) to provide regenerated aromatics solvent (13) and an aromatics stream (14). The regenerated aromatics solvent (13) may be used as the aromatics solvent used in the process and process installation of the present invention.
Figure 2:
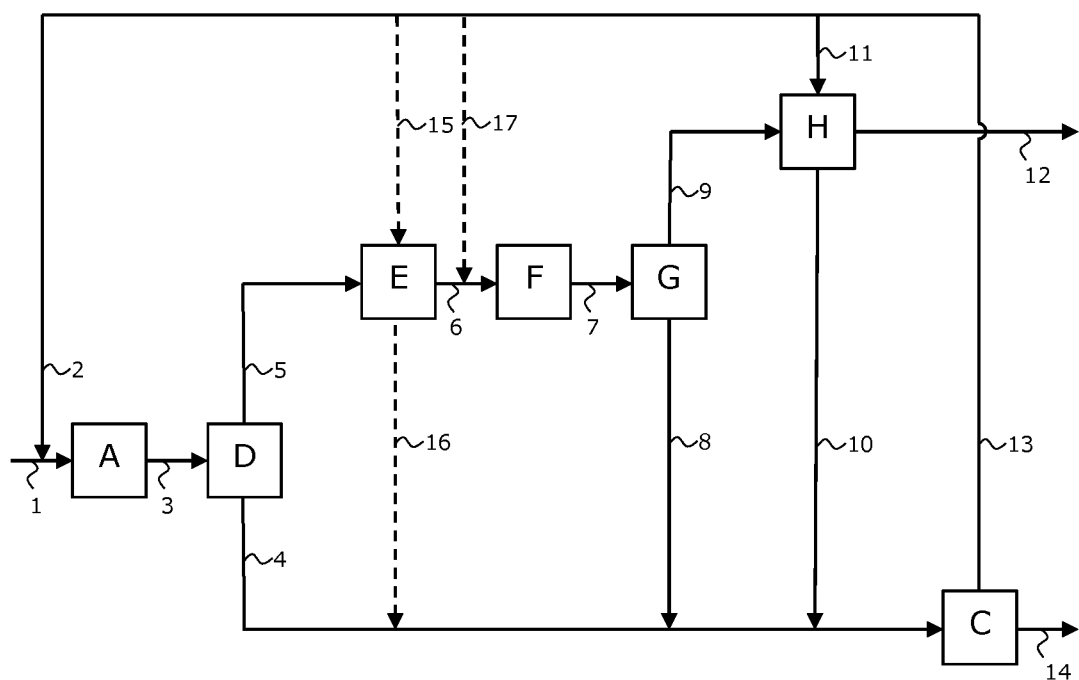
FIG. 2: More particularly, the separator (B) of FIG. 1 may comprise of different sub-steps, including gas-liquid separation, compression, cooling and aromatics absorption sub-steps. For instance, the separation may comprise a gas-liquid separation (D). The gaseous stream (5) that is obtained by the gas-liquid separation (D) may be subjected to compression, comprising one or more compression stages (E). The thus obtained compressed stream (6) may be subjected to further cooling in a compressed stream cooler (F) to provide a compressed and cooled stream (7) that may be subjected to a second gas-liquid separation (G) to provide a second aromatics-laden solvent stream (8) and a compressed gaseous stream obtained from second gas-liquid separation (9). The gaseous stream obtained from the first gas-liquid separation, optionally after being subjected to compression and/or cooling and/or a second gas-liquid separation as described above, may be fed to an aromatics absorption column (H) which further comprises an aromatics solvent feed (11) to produce a further (for instance a third) aromatics-laden solvent stream (10) and an effluent (12) that is substantially free of aromatics. As used herein, an effluent that is substantially free of aromatics comprises no more than 0.5 wt-% aromatics, preferably no more than 500 ppmw aromatics and most preferably no more than 50 ppmw aromatics. The ratio between naphthalene and aromatics solvent in the not yet condensed portion of the gaseous stream during the optional cooling and compression will shift towards naphthalene, if the aromatics solvent has a lower volatility than naphthalene, for instance which is the case for α-methyl naphthalene. This may create a combination of temperature, pressure and naphthalene content of the gas phase at which naphthalene may desublimate from the gas-phase or precipitate from the condensate although aromatics solvent is added upstream. Staged addition of aromatics solvent to the gaseous stream upstream of the aromatics absorption column, for instance via the aromatics solvent feed (15) to the partially compressed stream and/or the aromatics solvent feed (17) to the compressed stream, will ensure that the conditions which allow the deposition of solid naphthalene are avoided. All aromatics-laden solvent streams, for instance the aromatics-laden solvent stream (4) obtained from the first gas-liquid separator (D) and/or the aromatics-laden solvent stream (8) obtained from the second gas-liquid separator (G) and/or the aromatics-laden solvent stream (10) obtained from the aromatics absorption column (H) and/or the aromatics-laden solvent stream (16) obtained from the partially compressed stream from compressor (E), may be combined and subjected to solvent regeneration in solvent regeneration column (C) to provide regenerated aromatics solvent (13) and an aromatics stream (14).
Figure 3:
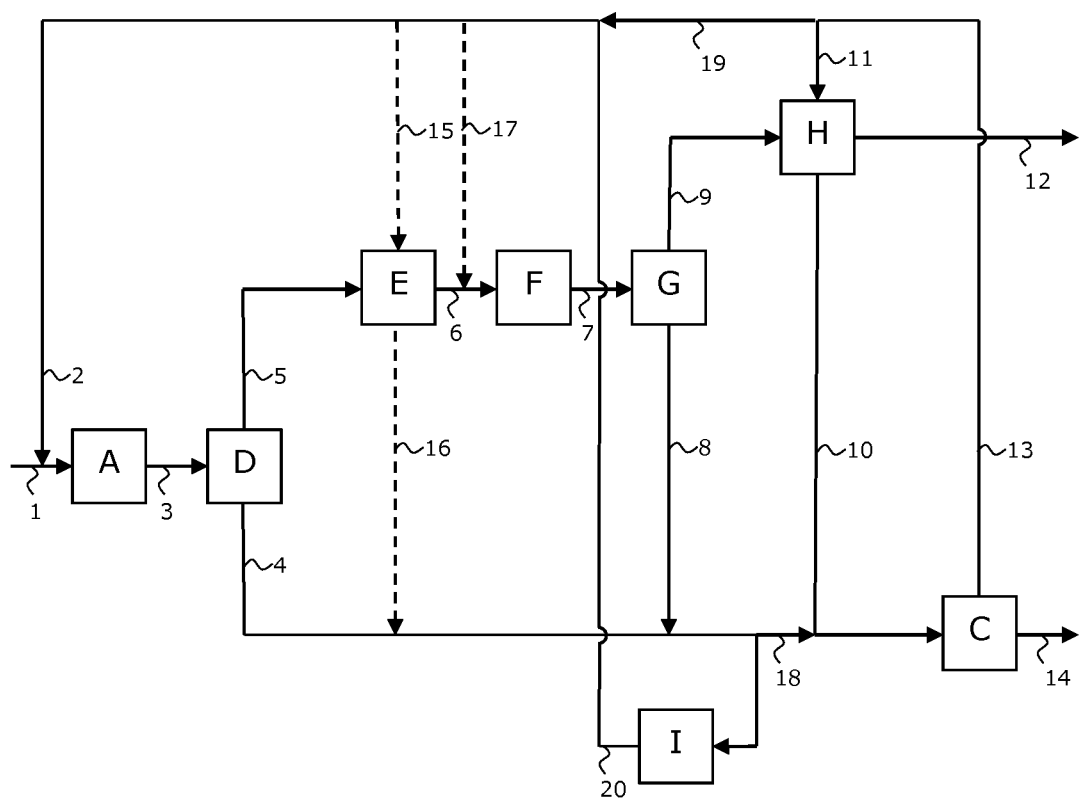
FIG. 3: More particularly, the aromatics solvent flow rate in stream (2) and/or stream (15) and/or stream (17) to the gaseous stream upstream of the aromatics absorption column (H) may be partially decoupled from the aromatics solvent absorption-regeneration loop originating from the aromatics absorption column by a short solvent cycle with the additional solvent cycle cooler (I). The liquid solvent-naphthalene mixture collected from the gas-liquid separators downstream of the effluent cooler(s), for instance the aromatics-laden solvent stream (4) obtained from the first gas-liquid separator (D) and/or the aromatics-laden solvent stream (8) obtained from the second gas-liquid separator (G) and/or the aromatics-laden solvent stream (16) obtained from the partially compressed stream from compressor (E), is cooled in cooler (I) and recycled to the aromatics solvent dosing points to the gaseous stream upstream of the aromatics absorption column such as via stream (2) and/or stream (15) and/or stream (17). Only a portion of naphthalene-laden solvent is returned to the solvent regeneration column via stream (18) and made up by regenerated solvent via stream (19). The portion of the naphthalene-laden solvent that is not returned to the solvent regeneration may be cooled and recycled to the process via stream (20).

The following alpha-numerical references are used in FIGS. 1-3 Units:
(A) Hydrocarbon-solvent mixture cooler
(B) Separator
(C) Solvent regeneration column
(D) First gas-liquid separator
(E) Compressor comprising one or more compression stages and optionally an intermediate gas-liquid separator
(F) Compressed stream cooler
(G) Second gas-liquid separator
(H) Aromatics absorption column
(I) Solvent cycle cooler Streams:
(1) Gaseous hydrocarbon feed stream
(2) Aromatics solvent feed to gaseous mixed hydrocarbon feed stream
(3) Cooled hydrocarbon-solvent mixture
(4) First aromatics-laden solvent stream
(5) Gaseous stream obtained from first gas-liquid separation
(6) Compressed stream
(7) Compressed and cooled stream
(8) Second aromatics-laden solvent stream
(9) Compressed gaseous stream obtained from second gas-liquid separation
(10) Third aromatics-laden solvent stream
(11) Aromatics solvent feed to aromatics absorption column
(12) Effluent that is substantially free of aromatics
(13) Regenerated aromatics solvent
(14) Aromatics stream
(15) Aromatics solvent feed to partially compressed stream
(16) Fourth aromatics-laden solvent stream
(17) Aromatics solvent feed to compressed stream
(18) Aromatics solvent return
(19) Aromatics solvent make-up
(20) Cooled aromatics solvent recycle

The invention claimed is:

1. Process for separation of aromatic hydrocarbons from a hydrocarbon feed stream comprising the steps of:
   (a) contacting a gaseous hydrocarbon feed stream comprising naphthalene with aromatics solvent to provide a gaseous hydrocarbon-solvent mixture;
   (b) reducing the temperature of the gaseous hydrocarbon-solvent mixture in a cooler to a temperature wherein the naphthalene co-condenses with the aromatics solvent and wherein the aromatics solvent is at least partially in liquid phase and the not absorbed hydrocarbons are in gas phase to obtain a cooled hydrocarbon-solvent mixture;
   (c) sending the thus obtained cooled hydrocarbon-solvent mixture to a separator and subjecting the thus obtained cooled hydrocarbon-solvent mixture to a separation in the separator to provide an aromatics-laden solvent stream and a gaseous stream; and
   (d) subjecting the aromatics-laden solvent stream to solvent regeneration to provide regenerated aromatics solvent and an aromatics stream.

2. The process according to claim 1, wherein step (a) comprises spraying liquid aromatics solvent into the gaseous hydrocarbon feed stream, wherein the gaseous hydrocarbon feed stream has a higher temperature than the aromatics solvent, thereby evaporating said aromatics solvent.

3. The process according to claim 1, wherein step (b) comprises reducing the temperature of the gaseous hydrocarbon-solvent mixture to 25-70° C.

4. The process according to claim 1, further comprising recycling the regenerated aromatics solvent obtained in step (d) to the aromatics solvent used in the process.

5. The process according to claim 1, wherein the aromatics solvent has a boiling point of 200° C. or more at ambient pressure.

6. The process according to claim 1, wherein the aromatics solvent is selected from the group consisting of methyl naphthalene, ethyl naphthalene, propyl naphthalene, di-methyl naphthalene, methyl ethyl naphthalene, di-ethyl naphthalene, methyl propyl naphthalene, ethyl propyl naphthalene, di-propyl naphthalene, tetralin, decalin, toluene, xylenes, decane, undecane, dodecane, tridecane, tetradecane and sulfolane.

7. The process according to claim 1, comprising producing the gaseous hydrocarbon feed stream by alkane aromatization.

8. The process according to claim 1, wherein the gaseous hydrocarbon feed stream comprises at least 1 wt-% aromatic hydrocarbons.

9. The process according to claim 1, further comprising contacting the gaseous stream with aromatics solvent in an aromatics absorption column to provide a further aromatics-laden solvent stream and an aromatics free effluent.

10. The process according to claim 9, further comprising recycling aromatics solvent provided by the solvent regeneration to the aromatics absorption column.

11. The process according to claim 1, wherein in step (c) the separation comprises gas-liquid separation.

12. The process according to claim 11, further comprising
subjecting the gaseous stream obtained by gas-liquid separation to a compression step followed by at least one cooling step, wherein the compression step comprises a first compression stage and contacting the partially compressed stream with aromatics solvent;
subjecting the thus obtained mixture to a second gas-liquid separation to provide a further aromatics-laden solvent stream and a partially compressed gaseous stream; and
subsequently subjecting the partially compressed gaseous stream to a second compression stage.

13. The process according to claim 11, further comprising
subjecting the gaseous stream obtained by gas-liquid separation to a compression step, and
subjecting the thus obtained compressed to a second gas-liquid separation to provide a further aromatics-laden solvent stream and a second gaseous stream.

14. The process according to claim 11, further comprising
subjecting the gaseous stream obtained by gas-liquid separation to a compression step with another subsequent cooling step, and
subjecting the thus obtained cooled and compressed stream to a second gas-liquid separation to provide a further aromatics-laden solvent stream and a second gaseous stream.

15. The process according to claim 11, further comprising
subjecting the gaseous stream obtained by gas-liquid separation to
at least one further cooling step;
and subjecting the thus obtained cooled or compressed, or optionally cooled and compressed stream to a second gas-liquid separation to provide a further aromatics-laden solvent stream and a second gaseous stream.

16. The process according to claim 15, further comprising
subjecting the gaseous stream obtained by gas-liquid separation to a compression step followed by at least one cooling step, wherein the thus obtained compressed and cooled stream has a pressure of 1500-4000 kPa.

17. A process for separation of aromatic hydrocarbons from a hydrocarbon feed stream comprising the steps of:
contacting a gaseous hydrocarbon feed stream with aromatics solvent to provide a gaseous hydrocarbon-solvent mixture;
reducing the temperature of the gaseous hydrocarbon-solvent mixture to a temperature wherein the aromatics solvent is at least partially in liquid phase and the not absorbed hydrocarbons are in gas phase;
subjecting the thus obtained cooled hydrocarbon-solvent mixture to a separation to provide an aromatics-laden solvent stream and a gaseous stream;
subjecting the aromatics-laden solvent stream to solvent regeneration to provide regenerated aromatics solvent and an aromatics stream;
subjecting the gaseous stream obtained by gas-liquid separation to a compression step followed by at least one cooling step; and
feeding additional aromatics solvent to the compressed stream between the compression step and the cooling step.

18. A process for separation of aromatic hydrocarbons from a hydrocarbon feed stream comprising the steps of:
contacting a gaseous hydrocarbon feed stream with aromatics solvent to provide a gaseous hydrocarbon-solvent mixture;
reducing the temperature of the gaseous hydrocarbon-solvent mixture to a temperature wherein the aromatics solvent is at least partially in liquid phase and the not absorbed hydrocarbons are in gas phase;
subjecting the thus obtained cooled hydrocarbon-solvent mixture to a separation to provide an aromatics-laden solvent stream and a gaseous stream;
subjecting the aromatics-laden solvent stream to solvent regeneration to provide regenerated aromatics solvent and an aromatics stream;
only partially subjecting one or more of the aromatics-laden solvent streams to solvent regeneration; and
cooling and recycling the remaining part of said one or more aromatics-laden solvent streams that are not subjected to solvent regeneration to the aromatics solvent used in the process.

19. The process according to claim 18, comprising using said remaining part of the one or more aromatics-laden solvent streams that are not subjected to solvent regeneration as the aromatics solvent feed.

* * * * *